(12) United States Patent
Xie (10) Patent No.: US 12,064,517 B1
(45) Date of Patent: Aug. 20, 2024

(54) POLYMER NANOPARTICLE

(71) Applicant: Hui Xie, New York, NY (US)

(72) Inventor: Hui Xie, New York, NY (US)

( * ) Notice: Subject to any disclaimer, the term of this patent is extended or adjusted under 35 U.S.C. 154(b) by 69 days.

(21) Appl. No.: 16/602,798

(22) Filed: Dec. 2, 2019

Related U.S. Application Data (60) Provisional application No. 62/917,381, filed on Dec. 3, 2018.

(51) Int. Cl.
| | |
|---|---|
| *A61P 35/00* | (2006.01) |
| *A61K 9/16* | (2006.01) |
| *A61K 9/19* | (2006.01) |
| *A61K 31/337* | (2006.01) |

(52) U.S. Cl.
CPC .............. *A61K 9/1652* (2013.01); *A61K 9/19* (2013.01); *A61K 31/337* (2013.01); *A61P 35/00* (2018.01)

(58) Field of Classification Search
CPC .......... A61K 9/19; A61K 9/1652; A61P 35/00
See application file for complete search history.

(56) References Cited

U.S. PATENT DOCUMENTS

| | | | | |
|---|---|---|---|---|
| 5,874,111 A | * | 2/1999 | Maitra ................. | A61K 9/5138 424/501 |
| 6,242,430 B1 | * | 6/2001 | Suzuki ............... | A61K 47/6951 536/103 |
| 9,522,197 B2 | | 12/2016 | Agüeros Bazo et al. | |

OTHER PUBLICATIONS

Kruti S. Soni et al., Nanogels: An overview of properties, biomedical applications and obstacles to clinical translation, J or Controlled Release, 240, 109-126. (Year: 2016).*

Ruxandra Gref et al. New self-assembled nanogels based on host-guest interactions: Characterization and drug loading, Journal of Control Release, 111, 316-324. (Year: 2006).*

Kruti S. Sone et al. Nanogels: an overview of properties, biomedical applications and obstacles to clinical translation, J Control Release, 240, 109-126. (Year: 2016).*

Mehmet Arslan et al. Fabrication of poly(ethylene glycol)-based cyclodextrin containing hydrogels via thiol-ene click reaction, European Polymer Journal, 62, 426-434. (Year: 2015).*

Markus J. Kettel et al. Aqueous nanogels modified with cyclodextrin, Polymer, 52, 1917-1924. (Year: 2011).*

Jianxiang Zhang et al. Cyclodextrin-based supramolecular systems for drug delivery: Recent progress and future perspective, Adv Drug Delivery Rev, 65, 1215-1233. (Year: 2013).*

Ke Peng et al. Cyclodextrin/dextran based drug carriers for a controlled release of hydrophobic drugs in zebrafish embryos, Sogf Matter, 6, 3778-3783. (Year: 2010).*

Xiaofei Chen et al. Dual responsive supramolecular nanogels for intracellular drug delivery, Chem. Co,,un, 50, 3789-3791. (Year: 2014).*

Jianxiang Zhang et al. Cyclodextrin-based supramolecular systems for drug delivery: Recent progress and future perspective, Adv Drug deli Rev. 65(9), 1-39. (Year: 2014).*

Zhi Liu et al. Oxidation-Induced Degradable Nanogels for Iron Chelation, Scientific Reports, 6, 20923 (1-9 pages). (Year: 2016).*

Feng Zhao et al. Supramolecular self-assembly forming a multifunctional synergistic system for targeted co-delivery of gene and drug, Biomaterials, 25, 1050-1062. (Year: 2014).*

Antonino Mazzaglia, Photodynamic Tumor Therapy with Cyclodextrin nanoassemblies, Cyclodextrin in Phamaceutics, Cosmetics, and Biomedicine, 18, 343-361. (Year: 2011).*

Xie, Hui Preparation of a β. Cyclodextrin Supramolecular Nanoparticles as a Drug Delivery System Published by FIT May 2014 in Melbourne, Florida.

* cited by examiner

*Primary Examiner* — Michael G. Hartley
*Assistant Examiner* — Jagadishwar R Samala
(74) *Attorney, Agent, or Firm* — Christopher Cappy (57) ABSTRACT

This invention provides a mono dispersed polymeric nanogel particle consists of a plurality of hydrophilic polymers or amphiphilic copolymers crosslinked with a plurality of cyclodextrin derivatives by sulfhydryl bonds. In some embodiments, the surface of the nanogel particle are attached with functional molecules, e.g., a cancer targeting ligand and a near-infrared dye. The polymeric nanogel particle can be made in aqueous solution at room temperature without organic additives via a continuous flow droplet reaction (CFDR™) method. The nanogel particle of this invention possesses internal pores, which can be used to encapsulate suitable compounds, particularly hydrophobic compounds to form stable colloidal dispersions in aqueous solution. Aspects of this invention include a method of inhibiting cancer cell growth.

19 Claims, 8 Drawing Sheets

FIG 1

TEM image of nanoparticle

UV-Vis spectrum of dye purpurin encapsulated in nanogel particle

POLYMER NANOPARTICLE

This application claims the priority of U.S. Provisional Patent Application No. 62/917,381 filed on Dec. 3, 2018 with the title, "Polymer Nanoparticle", and the content of which is incorporated herein by reference in its entirety.

FIELD OF THE INVENTION

The invention pertains to the field of polymeric nanogel, more particularly, a polymeric nanogel that can encapsulate and improve the aqueous solubility of suitable molecules. The invention also relates to the fields of targeted drug delivery and anticancer compounds.

BACKGROUND OF THE INVENTION

The efficient delivery of biologically active molecules to the target site is a key component for medication. It is well known that aqueous solubility, dissolution and gastrointestinal permeability are fundamental parameters that control drug absorption and in vivo bioavailability. Historically, it has been challenging to formulate hydrophobic drugs for parenteral application without the assistance of toxic organic co-solvents and surfactants such as tween, polysorbate and Cremophor. A large percentage of commercially available drugs, as well as those in clinical development have poor water/aqueous solubility. Many failures in new drug development can be attributed to the poor water solubility of the drug. Technology that can help improve the aqueous solubility of hydrophobic drugs is critical to achieving the ideal pharmacokinetics and pharmacodynamics profile of hydrophobic medications, as well as reduce their side effects.

Particulate polymer platforms, exemplified by nanogels or hydrogel nanoparticles, are some of the most ubiquitous platforms studied for the encapsulation of biologically active agents, with the goal of improving their water solubility, improving bioavailability and reducing side effects. Nanogels, encapsulating cargo compounds in their three dimensional interior mesopore or nanopore structures, form stable aqueous colloidal dispersions. Encapsulation with nanogels protects cargo compounds from degradation, early inactivation and dilution in the circulatory system, providing longer circulation time.

A well designed nanogel carrier can help deliver pharmacologically active agents to specific sites of interest by conjugation with a targeting ligand or due to passive targeting mechanisms, thus reducing toxicity and improving the therapeutic index. One mechanism for passive targeting of nanoparticles is the enhanced permeability and retention effect (EPR) of cancer tissues. Cancer angiogenesis produces new blood vessels around cancer tissues. The tumor's newly formed blood vessels are typically abnormal, exhibiting poorly aligned endothelial cells with wide fenestrations. The tumor tissues often lack lymphatic drainage. These and other factors result in the Enhanced Permeability and Retention (EPR) effect which allows nanoparticles of suitable size to accumulate in and at cancer tissue sites. With respect to the active targeting mechanism, ligands and cancer-specific cell surface markers conjugated to the surface of nanoparticles can facilitate active targeting of specific cancer cells by binding to the surface receptors. For example, the cell surface receptor for folic acid is often elevated in cancers of ovary, kidney, lung, breast, brain, and endometrium, and in myeloid cells of hematopoietic origin. The physicochemical properties of the nanoparticles determine their performance in biological systems. Particle size and particle size distribution are critical parameters for the pharmacokinetic and pharmacodynamic properties of nanoparticles. Homogeneous or mono dispersed polymer nanoparticles allow for better control of reproducibility of production and properties. It remains a challenge to produce homogeneous or mono dispersed polymeric nanoparticles due to the complexity of the synthetic methods available.

Despite the progress made in nanogel design, very few nanogels have been explored in clinical studies. Their intricate structural properties demand careful engineering. It can be challenging to fabricate nanogels that are capable of encapsulating substantially water insoluble agents. Hydrophobic modality can be fabricated into nanogels via grafting hydrophobic side chains and/or copolymerization with hydrophobic comonomers. These approaches, however, can cause deswelling and delocalized surface bulk hydrophobicity and potentially reduce the hydrophilicity, biocompatibility and/or the low protein binding properties of nanogels. It is critical to introduce functional modalities into the nanogel without compromising the hydrophilicity, yet enabling the encapsulation of agents with different physicochemical properties and/or the encapsulation of multiple agents. The modification of the nanogel surface with targeting ligands and/or other functional agents is of great interest to facilitate active targeting and other functionality, e.g. diagnostic imaging.

Safety is one of the major considerations when developing nanogels for clinical use. The preparation of nanogels usually requires the use of surfactants, initiators, organic solvents, emulsifiers etc. These chemicals, even if they only exist as trace impurities, can be toxic to human body. To remove these additives from the final product, costly downstream purification is required. The complex preparation process of nanogels remain a major challenge for developing a nanogel that is suitable for clinical applications.

SUMMARY OF THE INVENTION

The present invention provides a mono dispersed, biocompatible and biodegradable nanogel, comprising hydrophilic and/or amphiphilic polymers covalently crosslinked with cyclodextrins. In some of the embodiments, the surface of the nanogel comprise covalently linked, functional ligands such as tumor targeting ligands and a near infrared fluorescent dye. The nanogel particles of this invention can be in the form of a colloidal solution and/or a dry powder.

It has been discovered that the biocompatible and biodegradable nanogel particles of this invention have physicochemical characteristics suitable for the encapsulation of a wide variety of biologically active agents, particularly hydrophobic agents. The nanogel particles of this invention have the capacity to encapsulate large amounts of biologically active agents, improve their aqueous solubility, and potentially improve their bioavailability while reducing their overall toxicity.

In some embodiments, the nanogel particles comprise hydrophilic polymers and/or amphiphilic copolymers with internal biodegradable bonds selected from but not limited to ester bond, amide bond and disulfide bond. In some embodiments, the hydrophilic polymer is poly (ethylene glycol) (PEG).

In some embodiments, the nanogel particles comprise a plurality of β-cyclodextrin derivatives. In particular embodiments, the nanogel particles comprises a plurality of thiol-substituted β-cyclodextrin.

In some embodiments, the nanogel particles encapsulate a plurality of a biologically active agent such as hydrophobic drug, hydrophilic drug, biological product, cell, antibody, protein drug, nucleotide, imaging reagent, metal nanoparticle and etc.

One aspect of the invention includes the method to produce mono dispersed nanogel particles in aqueous solution at room temperature and ambient pressure. In some embodiments, the methods to make the mono dispersed nanogel particles comprise a Continuous Flow Droplet Reaction (CFDR™). This invention also provides a simple method to modify the mono dispersed nanogel particles with targeting ligands and other functional moieties under mild reaction conditions. In some embodiments, the synthetic process is without the assistance of surfactant, emulsifier, organic solvent or polymerization initiators. In some embodiments, the synthetic process is in aqueous solution at room temperature.

One aspect of the invention includes methods to encapsulate biologically active agents and other suitable compounds within the nanogel particles.

Yet another aspect of the invention includes methods for killing or inhibiting the growth or reproduction of cancer cells via the administration of nanogel particles encapsulated with chemotherapy agents to cancer cells.

DESCRIPTION

In the summary of the invention above and in the detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and the invention generally.

Where reference is made herein to a method comprising two or more defined steps, the defined steps can be carried out in any order or simultaneously (except where the context excludes that possibility), and the method can include one or more other steps which are carried out before any of the defined steps (except where the context excludes that possibility).

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

Definitions

Unless stated otherwise, technical and scientific terms used herein have the same meaning as commonly understood by one of ordinary skill in the art to which this invention belongs. For purposes of the present invention, the following terms are described below, "Nanogels" and "Nanogel Particles" include micron and submicron-sized nanoparticles with interior network formed by crosslink of the components disclosed in this invention. The particle of the invention generally has a mean particle size between 1 and 999 nanometers (nm), preferably between 10 and 900 nm.

"Mean size" refers to the mean diameter of the nanogel particle. The mean size of the nanogel particles can be measured by standard procedures known in the art and which are described, by way of illustration, in the experimental section.

"biocompatible" use herein refers to material components that are known to be nontoxic in mammalian tissues. Preferably, the material contains components that are categorized by FDA as "Generally Recognized as Safe" (GRAS).

"biodegradable" use herein refers to material that is able to degrade in a time period which is acceptable for the desired application under certain physiological conditions by means of glutathione reduction, hydrolysis, proteolysis and/or other related means.

"biologically active agent" includes without limitation, any therapeutic, palliative, cosmetic and/or prophylactic molecules, including without limitation, small molecules, drugs, biologicals, recombinant peptides, protein and nucleic acids and immunochemical molecules, as well as diagnostic and imaging compositions, as may be further indicated by the context. In some uses, the term can relate to other types of compositions, as indicated by the context.

"PDI" refers to the polydispersity index measured by dynamic light scattering method.

"mono dispersed" refers to nanoparticles with the PDI≤0.3. The PDI is measured by the dynamic light scattering method.

Detailed Description

Aspects of the invention include nanogel particles, having the components of 1) a plurality of hydrophilic polymers or amphiphilic copolymers that are soluble in aqueous solution; the polymers have one or a plurality of functional groups selected from but not limited to thiol, acrylate, methyl acrylate, maleimide or other functional groups that are capable of performing sulfhydryl crosslink chemistry; 2) a plurality of cyclodextrin derivatives, the cyclodextrin derivatives having one or a plurality of functional groups selected from but not limited to thiol, acrylate, methyl acrylate, or other functional groups that are suitable for sulfhydryl crosslink chemistry; 3) components 1 and 2 are crosslinked by thiol ether and/or disulfide bond; 4) the nanogel particles contains one or multiple types of biodegradable bonds; 5) the surface of the nanogel particles are optionally modified with functional agents such as targeting ligands and/or chromophores. The nanogels of this invention have particle size less than 200 nm, and are monodispersed (PDI≤0.3). The nanogel particles of this invention are essentially free of emulsifiers, organic solvents, photo initiators and surfactants.

Polyethylene glycol (PEG) is a synthetic, highly water soluble, inert polymer that is readily available in a wide range of molecular weights. PEG is one of the most widely used biocompatible hydrophilic polymers in fields such as drug delivery, tissue engineering, wound dressing and other consumer products. Chemical modification with PEG (PEGylation) is used to improve the pharmaceutical properties of therapeutic drugs. PEG is highly soluble in aqueous solution. When applied with bioactive molecules, PEG helps enhance the aqueous solubility. PEG has been used to improve the pharmaceutical properties of both small molecule and biotherapeutic drugs. PEG when associated with bioactive molecules, may help prolong circulation time of a protein or nucleic acid molecule, enhance aqueous solubility of drug substances, protect against in vivo biological inactivation by proteolysis, and reduce the immunogenicity of some biopharmaceuticals. The molecular weight of PEG used to form the nanogel particle in this invention ranges from around 200 Da to 200 k Da. In some embodiments, the molecular weight of the PEG ranges from about 200 Da to 10 k Da. In some embodiments, the molecular weight of the PEG ranges from about 1 k Da to 5 k Da. In some embodiments, the molecular weight of the PEG ranges from 1 k Da to 3.5 k Da. Suitable PEG includes but is not limited to linear PEG, branched PEG, multi-armed PEG and star-shaped PEG. The PEG in this invention has at least one functional group that is suitable for crosslink reaction. The functional groups are selected from but not limited to thiol, acrylate, methyl acrylate, succinimide, azide, maleimide, vinylsulfone and pyridyl disulfide. The PEG incorporated in this invention may be homo-functional or hetero-functional. In some embodiments, the PEG is PEG diacrylate. In some embodiments, the PEG is PEG dipyridyl disulfide.

It is understood by one ordinarily skilled in the art, that a variety of synthetic and natural hydrophilic polymers and copolymers can be incorporated in the nanogel particle of this invention. The hydrophilic polymer or copolymers can be in various molecular weights, and with at least one functional group suitable for the crosslink reaction. Examples of the hydrophilic polymers include but are not limited to poly vinyl alcohol (PVA), polyethylene glycol (PEG), polyethylenimine (PEI), polyoxazolines, and/or their copolymers thereof. Examples of the hydrophilic polymers can include natural hydrophilic polymers selected from but not limited to oligosaccharides, dextrins, gelatin, pectin, water soluble cellulose and polypeptide.

The nanogel particles disclosed in this invention comprise cyclodextrins. Cyclodextrins (CDs) are donut-shaped cyclic oligosaccharides. There are essentially three types of CDs, namely, α-cyclodextrin, β-cyclodextrin and γ-cyclodextrin that comprise of 6, 7 and 8 units of D-(+)-glucose respectively, linked by (1, 4)-α glycosidic bond. The cyclodextrin contains relatively hydrophobic cavities that are able to form host-guest complex with a variety of suitable molecules, while the hydrophilic rims of CDs allow for good aqueous solubility. The size of the cavities of the cyclodextrins are 0.56 nm, 0.70 nm and 0.88 nm for α-cyclodextrin, β-cyclodextrin and γ-cyclodextrin respectively, thus making them suitable different molecules for the formation of the host-guest complex. The cyclodextrins, particularly β-cyclodextrin (β-CD) and its derivatives, due to its affinity with wide variety of molecules, has been widely used as excipient in pharmaceutical and other industries to enhance the water solubility of guest molecules.

Native β-CD has the lowest solubility among all three CDs at 18.4 g/kg compared to 129.5 g/kg for α-cyclodextrin and 249.2 g/kg for γ-cyclodextrin. The low solubility of β-CD may be attributed to the intermolecular interaction at its crystalline state and the intramolecular hydrogen bonds between the secondary hydroxyl groups. Some β-CD derivatives have been prepared to improve the aqueous solubility of amorphous solids. The synthetic chemistry of CD modification has been extensively studied, and sophisticated methods to prepare the CD derivatives by modification of the CD hydroxyl groups are available in the literature. In some of the embodiments of this invention, the CD derivatives used for the nanogel particles are thiol substituted CD. The thiol groups can locate on either the 2, 3 or 6 positions of the glucose units. At least one hydroxyl group is substituted by desirable functional groups for the crosslink reaction. Preferably, the substitution is on the 6-hydroxyl groups. The substitution groups are selected from but not limited to azide, thiol, acrylate, amine and other functional groups that can facilitate a crosslink reaction with a functionalized hydrophilic polymer. In some embodiments, the substitution is for all 6-hydroxyl groups. In some embodiments, the CD derivative is 6-deoxy-heptakis-thiol-β-CD.

Cyclodextrins and their derivatives are biocompatible, and have been approved for use as excipient in drug products. CDs, like starch, are degradable in human body by amylase hydrolysis via the breakage of 1,4-α glycosidic bond.

Figure 1:
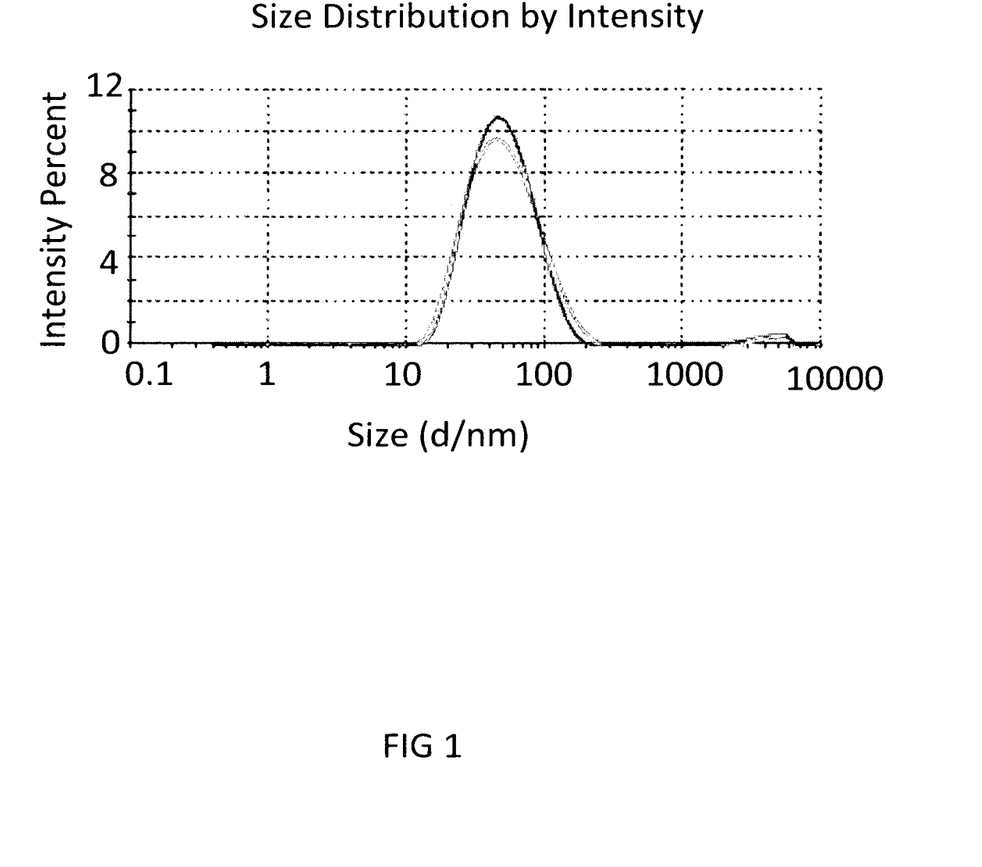
FIG. 1. shows an example of the average particle size measured by dynamic light scattering.
Figure 2:
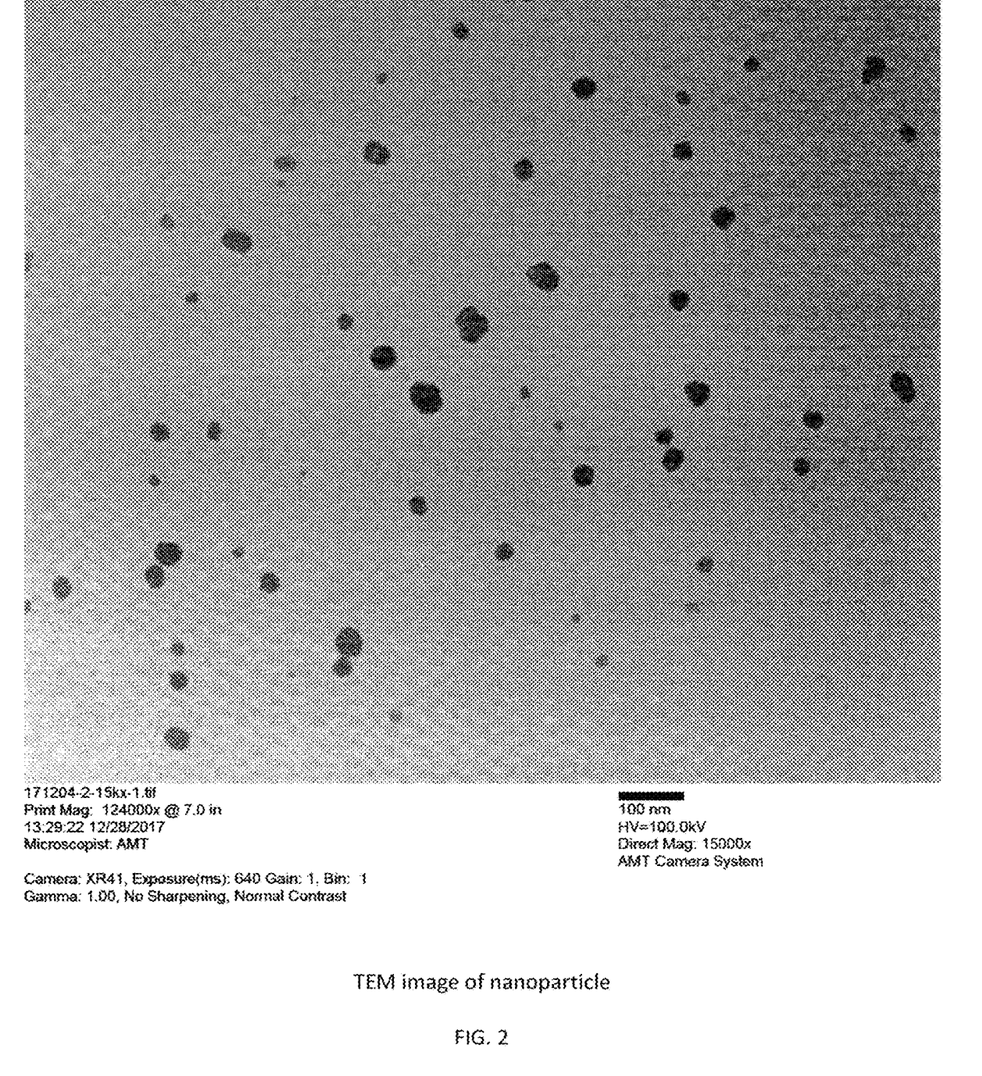
FIG. 2. shows an example of the transmission electronic microscope (TEM) image of the nanoparticles.
Figure 3:
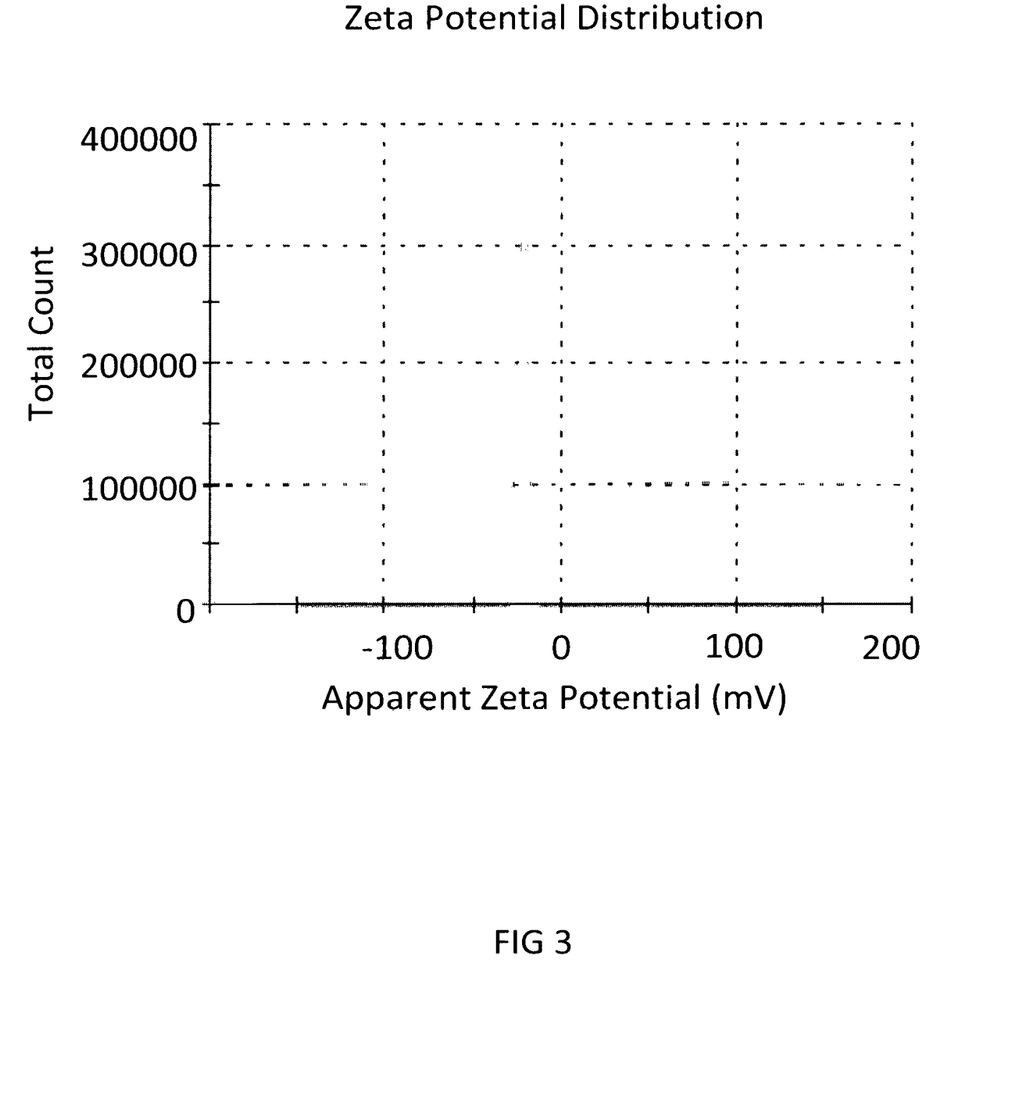
FIG. 3. shows an example of the zeta potential of the nanoparticles of this invention.
Figure 4:
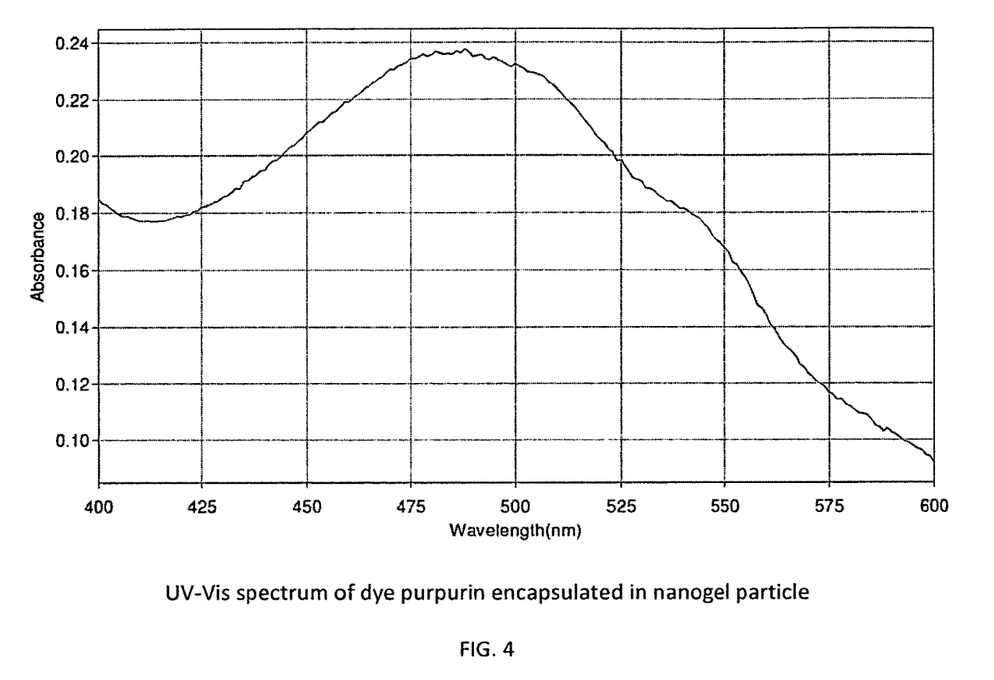
FIG. 4. shows the UV-Vis spectrum of a nanogel encapsulated with the dye purpurin.
Figure 7:
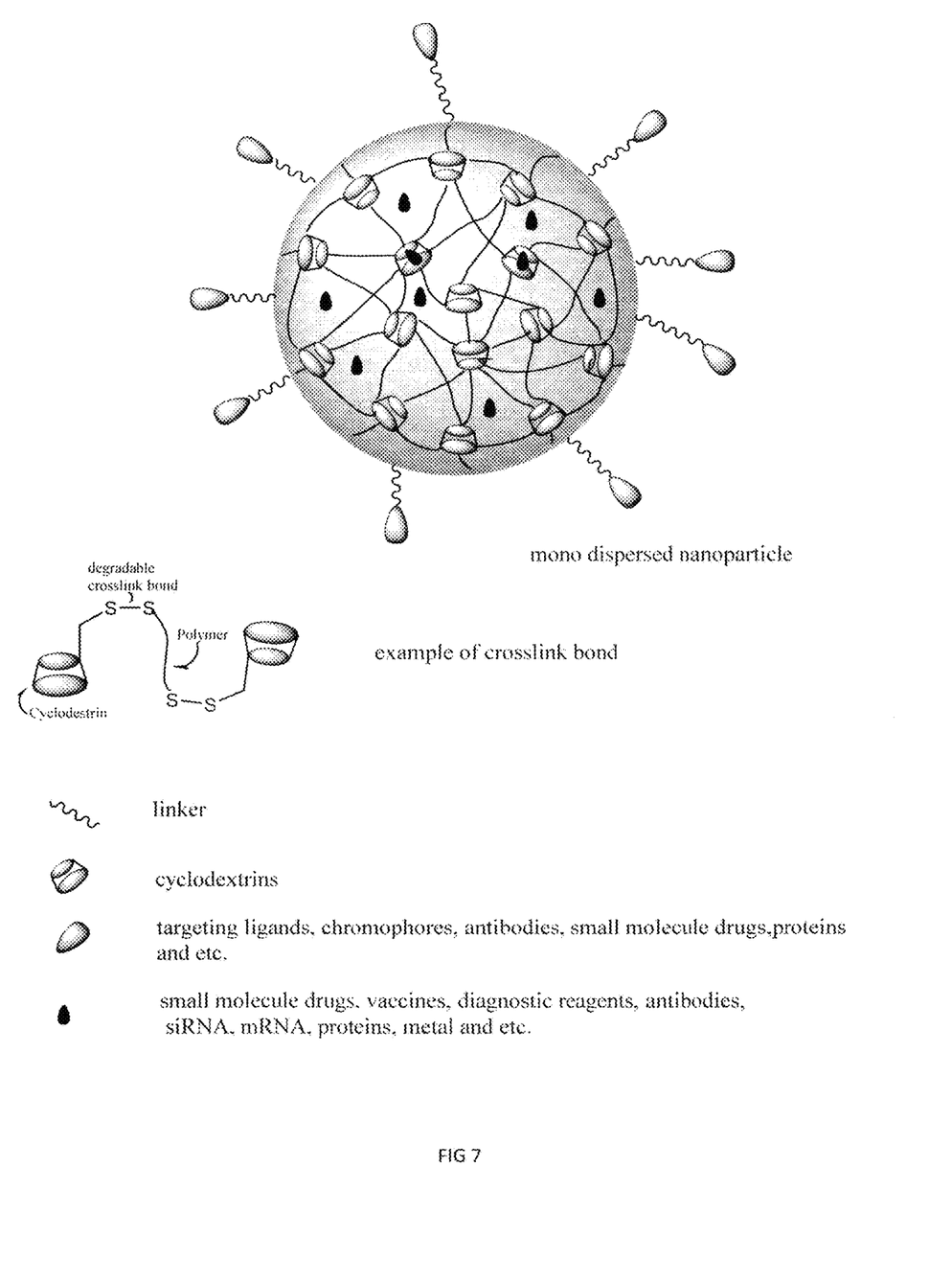
FIG. 7. shows the illustration of the structure of the nanogel particle of this invention.

The nanogel particle disclosed in this invention comprises a core-shell structure as shown by the TEM image, in contrast to the normal nanogel structures known in the art where the components are dispersed throughout the volume of the microsphere. The nanogel particle disclosed in this invention has the more hydrophilic chain appearing at the shell while the relatively more hydrophobic cyclodextrin moiety is found in the core. This is the result of self-assembly of the nanogel particles occurring simultaneously with the crosslink reaction. The completion of the crosslink gives rise to an amphiphilic polymer, which in turn, self-assembles spontaneously, leaving the hydrophilic polymer at the shell, with the hydrophobic moiety and cyclodextrin moiety in the core. Therefore, the nanogel particle of this invention can be a novel and simple "PEGylation" tool for biologically active agents by a cost effective, simple physical encapsulation under mild conditions with a high drug/polymer ratio. Traditional "PEGylation", on the other hand, requires covalent bonding of the agents to the polymer. It would understood by one with ordinary skill in the art that this is a simple and cost effective alternative to the traditional "PEGylation". The nanogel particles are readily dispersed in aqueous solution forming colloidal systems. The hydrophilic shell comprising PEG can also provide immune-stealth effects when the nanoparticles are circulating in blood stream, which may facilitate longer circulation time for the nanoparticles and the cargo they carry.

The nanogel particles are biodegradable. In some embodiments, the crosslinking bonds are biodegradable bonds selected from but not limited to disulfide bond, ester bond and amide bond. The biodegradation of the nanogel particles can be the result of the breakage of one or multiple types of bonds selected from but not limited to disulfide bond, ester bond, amide bond, lactone bond and epoxide bond. In some embodiments, the biodegradation of the nanogel particles can be a result of the breakage of the disulfide bond by the glutathione reduction, which is related to the glutathione concentration in cells. In some embodiments, the biodegradation of the nanogel particles can be a result of the hydrolysis of ester or amide bonds present in the nanoparticle, a process that is sensitive to pH and the presence of enzyme. In some embodiments, the biodegradation of the nanogel particle can be attributed to the presence of both the disulfide bond and ester bond. One of ordinary skill in the art should recognize that a variety of biodegradable bonds, stimuli responsive functional groups and stimuli responsive polymers such as poly (N-isopropylacrylamide) (PNIPAM) can be incorporated into the nanogel particle of the invention to render variable degradation or a morphology change profile. Thus, the nanogel particles can be a flexible scaffold to deliver cargos and release them by bond breakage or morphology change under desirable environmental conditions.

Particle size and particle size distribution (PDI) decide the distribution and availability of nanoparticles and the agents they carry. The in vitro and in vivo properties of nanoparticles depend on their physical and chemical properties, including particle size and size distribution, surface morphology, surface charge, steric stabilization, drug loading efficiency and drug release kinetics. It is widely accepted that particle size and size distribution is one of the most critical characteristics that impact the pharmacokinetics, pharmacodynamics and safety of nanoparticle based medicines. After administration, nanoparticles with a size between 20 nm-30 nm are quickly filtered out by renal system, while nanoparticles 200 nm or bigger are efficiently taken up by mononuclear phagocytic system (MPS). To achieve the full benefit of nanomedicine, the nanoparticle should have a mean particle size less than 200 nm.

The nanogel particles disclosed in this invention may have any suitable sizes. The nanogel may have a diameter from about 3 nm to about 30 nm, about 30 nm to 100 nm, about 50 nm to 100 nm, about 100 nm to about 200 nm, about 200 nm to about 1000 nm. Preferably, for in vivo delivery of biological active reagents, the particles will have a diameter from about 30 nm to about 200 nm. The size of the nanogel particle varies as required by the particular use. For example, to deliver drugs to cancer tissue, the nanogel particle size should be less than 200 nm. The nanogel particles disclosed in this invention are mono dispersed and/or homogeneous.

The nanogel particles disclosed in this invention may be incorporated with surface functional modalities such as targeting ligands for in vivo targeting and fluorescent dye for tracking of the particles. In one embodiment, the targeting ligand is folate. In some embodiments, the surface of the nanogel particles can be modified with more than one modalities, e.g. a targeting ligand and a chromophore.

The nanogel particles of the invention can be dried by a variety of means such as freeze drying and spray drying. The dried powder of the nanogel with or without cargo can be readily reconstituted to a colloidal dispersion at any desirable concentration without the changing of the particle size or morphology. Therefore, the nanogel particle can be used to formulate the biologically active agent for a range of a drug administration pathways such as parenteral administration, oral administration, ophthalmic administration, nasal administration, pulmonary administration and etc.

The simplicity of the synthetic method is desirable for repeatable, cGMP manufacturing of the nanoparticle material. The major hinderances for the development of nanogels lies greatly in the complexity and high cost of the synthetic and purification process. The synthetic methods available in the art usually need the help of emulsifiers, surfactants, initiators and organic solvents. In some embodiments of this invention, the nanogel particles are prepared by a simple and green process in aqueous solution at room temperature and ambient pressure without additional surfactant, emulsifier, initiator and/or organic solvent. One with ordinary skill in the art would understand that the downstream purification to produce this nanogel material useful for clinical application would become simple.

Figure 8:
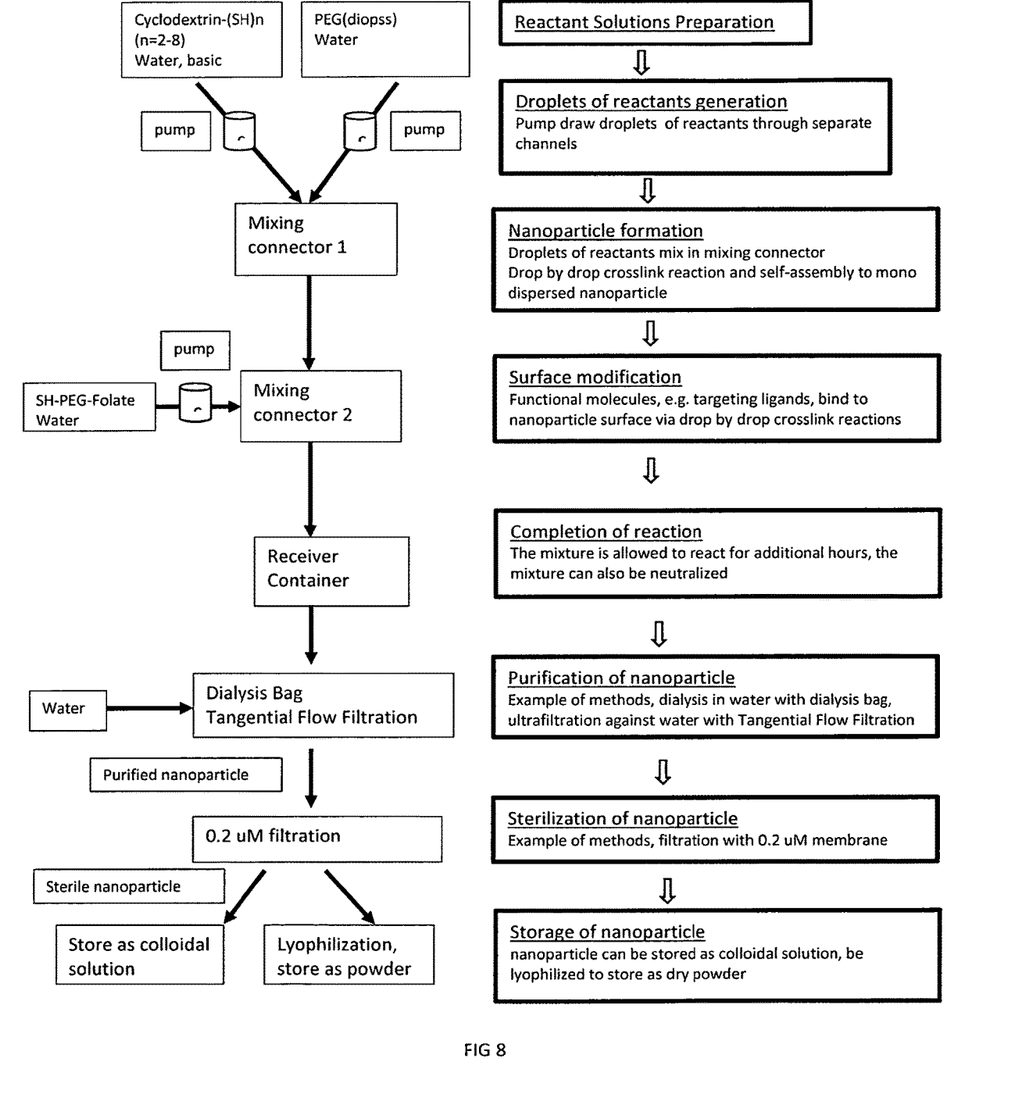
FIG. 8. shows the flowchart of continuous flow droplet reaction (CFDR) method to make the nanogel particle of this invention.

In some embodiments of this invention, a Continuous Flow Droplet Reaction (CFDR™) was used to fabricate the nanogel particles. In some embodiments, the method is used to fabricate mono dispersed nanogel particles. The general procedure for the CFDR method comprise the use of pump means to drive reactants in solution into separate channels so that the droplets of each reactant arrive simultaneously at a mixing connector, and are mixed drop-by-drop at a suitable speed to allow the polymerization and simultaneous self-assembly in order to form nanoparticles, the mixture then continues to be pumped through a channel, and dropped into a receiver container. In some embodiments, the CFDR™ method result in mono dispersed nanogel particles. In some embodiments, the reaction was carried out in room temperature and aqueous solution without initiators, emulsifiers and organic solvents. In some embodiments of this invention, suitable microfluidic devices can be employed as the mixing connector. One of ordinary skill in the art would recognize that the CFDR™ method can be used to manufacture large quantities of homogenous, mono dispersed nanogel particles with controlled and reproducible properties.

In some embodiments of this invention, methods are provided for modification of the surface of the nanogel particles with different functional molecules, e.g. targeting ligands and/or chromophore. In some embodiments, the functional molecules are attached to the surface of the nanogel particles by covalent bonding to the free functional group on the surface of the nanogel particles. In some embodiments, the reaction solution of the functional molecules is dropped into the receiver container containing nanogel particles to allow the covalently bonding. In some embodiments, additional channels of the reaction solutions of functional molecules are incorporated in the CFDR™, e.g. additional pump means to draw the reaction solutions of functional molecules to drop simultaneously with the nanogel particle droplet in additional mixing connectors at a suitable speed to allow covalent bonding, the mixture is then pumped through a channel, and dropped into a receiver container. One of ordinary skill in the art would recognize that this invention provides a process under mild conditions that is suitable to attach sensitive functional molecules such as antibody, peptide etc. without altering their properties.

Nanogels are highly crosslinked and porous materials, easily trapping organic agents introduced during production. In some embodiments, the process to make the nanogel particles of this invention are essentially free of organic solvents, emulsifiers, initiators and detergents. In some embodiments, the nanogel particles are purified using dialysis bags of suitable material, e.g. PTFE and/or regenerated cellulose and suitable molecular weight cutoffs. One of ordinary skill in the art would recognize all the suitable purification methods in the art that can be employed to purify the nanogel particles of this invention, e.g. tangential flow filtration (TFF), gel permeation chromatography (GPC)/size exclusion chromatography (SEC) and/or ultracentrifuge. In some embodiments, the nanogel particles are further sterilized by suitable methods, e.g., filtration through filters with a pore size less than 0.22 µM.

One of ordinary skill in the art would recognize other suitable methods in the art that can be used to sterilize the nanogel particles of this invention.

The nanogel particles of this invention are highly crosslinked polymers that comprise an interior network and a cyclodextrin cavity to load suitable cargos. The nanogel particles of this invention can encapsulate suitable biologically active agents by various molecular interactions such as van der wall force, dipole-dipole moment, pi-pi interaction, hydrogen bond, hydrophobic interaction, ionic interaction etc. There are two types of interior cavities that can encompass suitable guest molecules, the cavities of cyclodextrins and the pores resulting from the crosslink reaction. Thus, the nanogel particles of this invention have the capacity to associate with a variety of biologically active agents with a high loading ratio. The guest molecular cargo may be any suitable molecules and/or material. The molecules that are suitable may be selected from, but are not limited to small molecule drugs, antibody, vaccine, diagnostic reagent, imaging reagent, oligonucleotide, polypeptide, nutrition supplement, cosmetic reagent, metal semiconductor, metal nanoparticle and quantum dots. In some embodiments of this invention, the cargos are hydrophobic drugs. In some embodiments, the cargos are hydrophilic drugs. In some embodiments, the cargos are amphiphilic molecules. In some embodiments, the cargos are a proteins. In some embodiments, the cargos are anticancer drugs. The guest molecular cargos are encapsulated into the nanogel particles by physical interactions. In other aspects, the guest molecular cargos can be loaded to the surface of the nanogel particles by means of chemical bonding and physical interactions. The guest molecular cargos may be loaded in any suitable amount. The loading methods of the molecular cargo to the nanogel can be any of the methods developed in the art for molecular encapsulation. For example, the cargo can be loaded by freeze drying method, slurry method, spray dry method etc. One embodiment of this invention discloses a method of encapsulation comprising lyophilization drying of the mixture nanogel particles and the cargo compounds.

Example 1

Preparation of PEG Di(Opss) Crosslinked Nanogel

Seventy three mg of PEG di(opss) with MW 1000 (Nanosoft Polymers) was added to a 20 ml glass vial, 4 ml of di water was added to the vial, the mixture was stirred to completely dissolve the PEG di(opss). Twenty five mg of 6-deoxy-heptakis-thiol-$\beta$-CD (Cycodextrin Shop) was added to a 20 ml glass vial, 4 ml of di water was added, followed by NaOH (2M, 0.5 ml), the mixture was stirred to completely dissolve the cyclodextrin. The two solutions were loaded into two 10 ml gas tight glass syringe (Hamilton) separately, and the two syringes were then loaded to a syringe pump (Harvard Pump). The solutions were dropped through a three way Y shape plastic connector into a 20 ml reaction vial over 1 hour. The resulting mixture was set aside in the vial for 2 hours, and then stirred using magnetic stirring bar overnight. HCl (2M) was dropped into the mixture to neutralize the mixture. The mixture was then transferred into a dialysis bag (regenerated cellulose, MWCO 3500) to dialysis against di-water for 24 hours. The final solution was transferred into 20 ml glass vials, and filtered by PTFE 0.2 μm syringe filter (Whiteman) and dried by freeze-drier to achieve white powder.

Dynamic Light Scattering (DLS) Malvern, Nano S Zetasizer is used to characterize the particle size and zeta potential of the nanogel particles. For particle size measurement, the nanogel sample solution was prepared by dissolving the dry powder of nanogel with di water to make a stock solution at the concentration of 1 mg/ml. The stock solution was diluted ten times to obtain the testing solution Transmission Electronic Microscopy (JOEL 1010 transmission electron microscope 100 Key coupled with AMT XR41-B4-megapixel (2048) bottom mount CCD camera) is also used to characterize the particle size and morphology of the nanogel. The samples were prepared by dropping the sample solution onto a Copper Grid (FORMVAR film on 200 square mesh copper grids)

Example 2

Preparation of PEG Di(Opss) Crosslinked and Folate Modified Nanogel

Eighty five mg of PEG di(opss) (Nanosoft Polymers, MW 1000) was added to a 20 ml glass vial, 4 ml of di water was added to the vial, the mixture was stirred to completely dissolve the PEG di(opss). Twenty five mg of 6-deoxy-heptakis-thiol-$\beta$-CD (Cycodextrin Shop) was added to a 20 ml glass vial, 4 ml of di water was added, followed by NaOH (2M, 0.5 ml), the mixture was stirred to completely dissolve the cyclodextrin. The two solutions were loaded to two 10 ml gas tight glass syringe (Hamilton) separately, and the two syringes were then loaded to a syringe pump (Harvard Pump). The solutions were dropping through a three way Y shape plastic connector into a 20 ml reaction vial over 1 hour. Ten mg of Folate-PEG-SH (Biochempeg, MW 1000) was added to a glass vial, 1 ml of di water was added to the vial followed by 0.1 ml of NaOH (2M) to completely dissolve the solid. The solution was dropped to reaction vial. The resulted mixture was set aside in the vial for 2 hours, and then stirred using magnetic stirring bar overnight. HCl (2M) was dropped into the mixture to neutralize the mixture. The mixture was then transferred into a dialysis bag (regenerated cellulose, MWCO 3500) to dialysis against di-water for 24 hours. The final solution was transferred into 20 ml glass vials, and filtered by 0.2 μm syringe filter (Whiteman) and dried by freeze-drier to achieve white powder.

Dynamic Light Scattering (DLS) Malvern, Nano S Zetasizer is used to characterize the particle size and zeta potential of the nanogel particles. For particle size measurement, the nanogel sample solution was prepared by dissolving the dry powder of nanogel with di water to make a stock solution at the concentration of 1 mg/ml. The stock solution was diluted ten times to obtain the testing solution Transmission Electronic Microscopy (JOEL 1010 transmission electron microscope 100 Kev coupled with AMT XR41-B4-megapixel (2048) bottom mount CCD camera) is also used to characterize the particle size and morphology of the nanogel. The samples were prepared by dropping the sample solution onto a Copper Grid (FORMVAR film on 200 square mesh copper grids)

Example 3

Preparation of PEG Diacrylate Crosslinked and Folate Modified Nanogel

Eighty five mg of PEG diacrylate (Polyscience, MW 1000) was added to a 20 ml glass vial, 4 ml of di water was added to the vial, the mixture was stirred to completely dissolve the PEG di(opss). Twenty five mg of 6-deoxy-heptakis-thiol-$\beta$-CD (Cycodextrin Shop) was added to a 20 ml glass vial, 4 ml of di water was added, followed by NaOH (2M, 0.5 ml), the mixture was stirred to completely dissolve the cyclodextrin. The two solutions were loaded to two 10 ml gas tight glass syringe (Hamilton) separately, and the two syringes were then loaded to a syringe pump (Harvard Pump). The solutions were dropping through a three way Y shape plastic connector into a 20 ml reaction vial over 1 hour. Ten mg of Folate-PEG-SH (Biochempeg, MW 1000) was added to a glass vial, 1 ml of di water was added to the vial followed by 0.1 ml of NaOH (2M) to completely dissolve the solid. The solution was dropped to reaction vial. The resulted mixture was set aside in the vial for 2 hours, and then stirred using magnetic stirring bar overnight. HCl (2M) was dropped into the mixture to neutralize the mixture. The mixture was then transferred into a dialysis bag (regenerated cellulose, MWCO 3500) to dialysis against di-water for 24 hours. The final solution was transferred into 20 ml glass vials, and filtered by PTFE 0.2 μm syringe filter (Whiteman) and dried by freeze-drier to achieve white powder.

Dynamic Light Scattering (DLS) Malvern, Nano S Zetasizer is used to characterize the particle size and zeta potential of the nanogel particles. For particle size measurement, the nanogel sample solution was prepared by dissolving the dry powder of nanogel with di water to make a stock solution at the concentration of 1 mg/ml. The stock solution was diluted ten times to obtain the testing solution Transmission Electronic Microscopy (JOEL 1010 transmission electron microscope 100 Kev coupled with AMT XR41-B4-megapixel (2048) bottom mount CCD camera) is also used to characterize the particle size and morphology of the nanogel. The samples were prepared by dropping the sample solution onto a Copper Grid (FORMVAR film on 200 square mesh copper grids)

Example 4

Preparation of PEG Diacrylate Crosslinked and FITC Modified Nanogel

Eighty five mg of PEG diacrylate (Polyscience, MW 1000) was added to a 20 ml glass vial, 4 ml of di water was added to the vial, the mixture was stirred to completely dissolve the PEG di(opss). Twenty five mg of 6-deoxy-heptakis-thiol-β-CD (Cycodextrin Shop) was added to a 20 ml glass vial, 4 ml of di water was added, followed by NaOH (2M, 0.5 ml), the mixture was stirred to completely dissolve the cyclodextrin. The two solutions were loaded to two 10 ml gas tight glass syringe (Hamilton) separately, and the two syringes were then loaded to a syringe pump (Harvard Pump). The solutions were dropping through a three way Y shape plastic connector into a 20 ml reaction vial over 1 hour. Ten mg of FITC-PEG-SH (Biochempeg, MW 2000) was added to a glass vial, 1 ml of di water was added to the vial followed by 0.1 ml of NaOH (2M) to completely dissolve the solid. The solution was dropped to reaction vial. The resulted mixture was set aside in the vial for 2 hours, and then stirred using magnetic stirring bar overnight. HCl (2M) was dropped into the mixture to neutralize the mixture. The mixture was then transferred into a dialysis bag (regenerated cellulose, MWCO 3500) to dialysis against di-water for 24 hours. The final solution was transferred into 20 ml glass vials, and filtered by PTFE 0.2 μm syringe filter (Whiteman) and dried by freeze-drier to achieve white powder.

Dynamic Light Scattering (DLS) Malvern, Nano S Zetasizer was used to characterize the particle size and zeta potential of the nanogel particles. For particle size measurement, the nanogel sample solution was prepared by dissolving the dry powder of nanogel with di water to make a stock solution at the concentration of 1 mg/ml. The stock solution was diluted ten times to obtain the testing solution Transmission Electronic Microscopy (JOEL 1010 transmission electron microscope 100 Kev coupled with AMT XR41-B4-megapixel (2048) bottom mount CCD camera) is also used to characterize the particle size and morphology of the nanogel. The samples were prepared by dropping the sample solution onto a Copper Grid (FORMVAR film on 200 square mesh copper grids)

Example 5

Encapsulation of Purpurin Dye 6 mg of PEG diacrylate (MW 1000) β-cyclodextrin crosslinked nanogel was dispersed in 3 ml of di water, 2 mg of purpurin solid was added to the solution. The resulted mixture was stirring overnight. The purpurin was found to dispersed in the aqueous as a transparent colloidal solution.

Example 6

Preparation of Nanogels Encapsulated with Paclitaxel

The nanogels encapsulate paclitaxel were prepared by lyophilization method. Generally, paclitaxel (Cayman Chemical) was dissolved in ethyl alcohol, and the nanogel was dissolved in di water, and the paclitaxel solution was mixed with the nanogel aqueous solution, and the mixture was lyophilized to achieve the nanogels encapsulated with paclitaxel as white powder.

Three nanogels encapsulated with paclitaxel were prepared according to the following table. The lyophilized powders were find to be able to dissolve in di water forms clear solution, which indicate the encapsulation of the hydrophobic drug paclitaxel.

| Sample ID | Sample | Weight of nanogel | Weight of paclitaxel | Encapsulation percentage |
| --- | --- | --- | --- | --- |
| SY2019-CH001 | PEG diacrylate 1000-β-CD-folate | 11 mg | 1.9 mg | 14.7% |
| SY2019-CH002 | PEG diacrylate 1000-β-CD | 11 mg | 2.5 mg | 18.5% |
| SY2019-CH003 | PEG di (opss) 1000-β-CD | 9 mg | 2.5 mg | 21.7% |

Example 7

In Vitro Efficacy $IC_{50}$ Cancer Cell Line Test for Nanogels Encapsulated with Paclitaxel The antiproliferative activity was studied against human tumor cell lines, Human Lung Carcinoma A549 and Human Mammary Gland Adenocarcinoma MCF-7 with Promega's Cell Tier-Glo® Luminescent Cell Viability assay.

A preliminary cell titration was conducted to select the proper seeding density for the growth of these lines for the relevant time frames.

The tumor cells were seeded in a volume of 90 μL/well of growth medium into a white polystyrene 96-well microculture plate (Corning® Costar® 96-well flat bottom plate, Cat #3917). After 24 hours of incubation in a humidified incubator at 37° C., in an atmosphere of 5% $CO_2$ and 95% air, 10 μL of 10 serially diluted test agent in growth medium were added to each well in duplicate (10 points dose response, highest concentration 0.4 μM, with a 1:2 dilution plus untreated control). After 72 hours of culture with test article, in a humidified incubator at the atmosphere of 5% $CO_2$ and 95% air, the plate cells and Cell Titer-Glo® (Promega G7571) reagents were brought to room temperature to equilibrate for 30 minutes. 100 μL of Cell Titer-Glo® (Promega G7571) reagent was added to each well. The plates were shaken for two minutes and then left to equilibrate for ten minutes prior to reading luminescence on the Biotech Synergy II microplate reader. The $IC_{50}$ results are listed in the following tables and are shown in graphs in FIG. 5 and FIG. 6.

Figure 5:
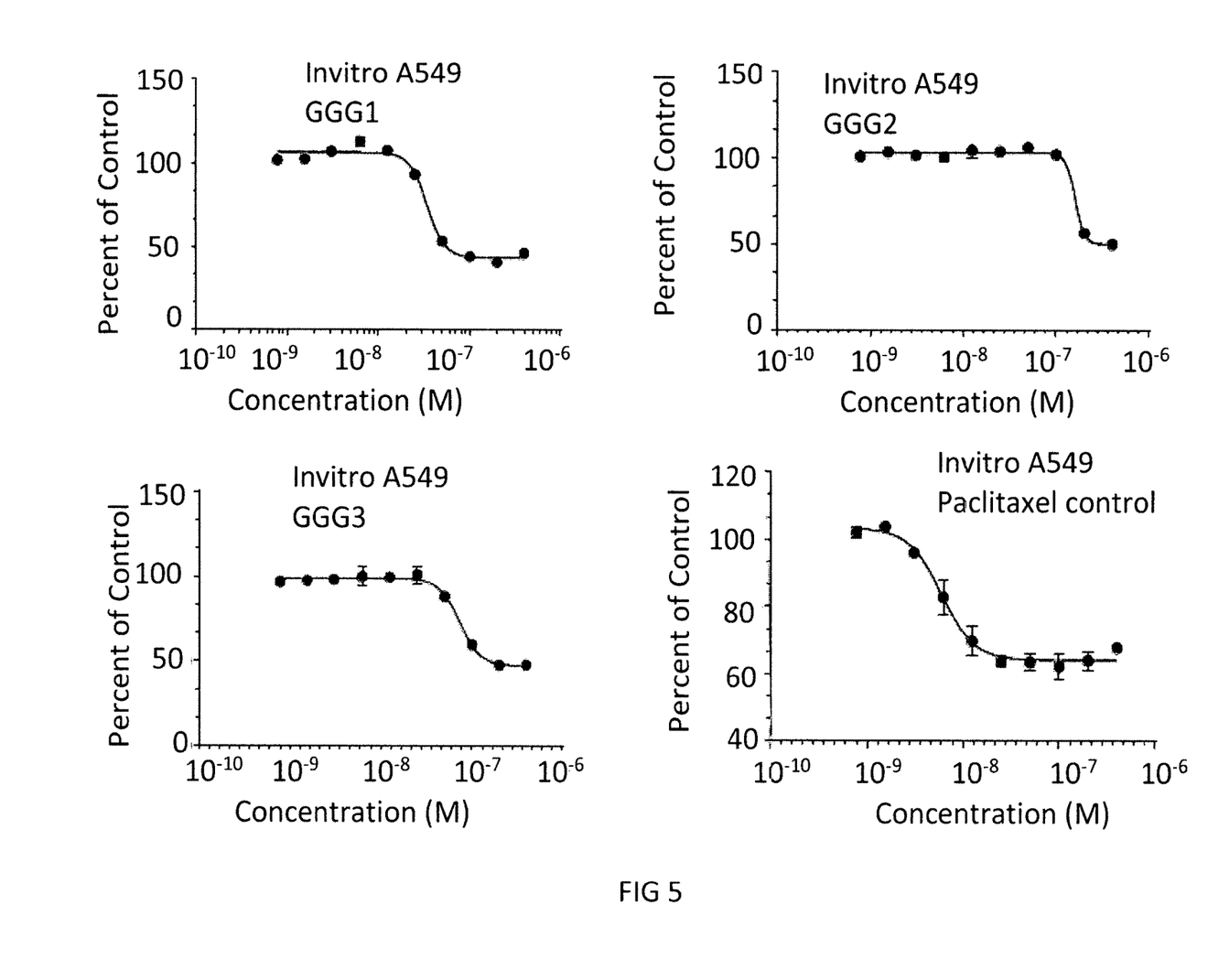
FIG. 5. shows the $IC_{50}$ of human lung cancer A549 cell line for three nanogels encapsulated with paclitaxel and the paclitaxel control.

| A549 cell line | | | | |
|---|---|---|---|---|
| Sample Name | Test ID | $IC_{50}$ | Curve Fit Parameter $R^2$ of fit | Plate Statistics Z' |
| SY2019-CH001 | GGG1 | $3.410 \times 10^{-8}$ | 0.987 | 0.98 |
| SY2019-CH002 | GGG2 | $1.592 \times 10^{-7}$ | 0.989 | 0.98 |
| SY2019-CH003 | GGG3 | $7.316 \times 10^{-8}$ | 0.988 | 0.90 |
| Paclitaxel Control | | $5.979 \times 10^{-9}$ | 0.975 | 0.90 |

Figure 6:
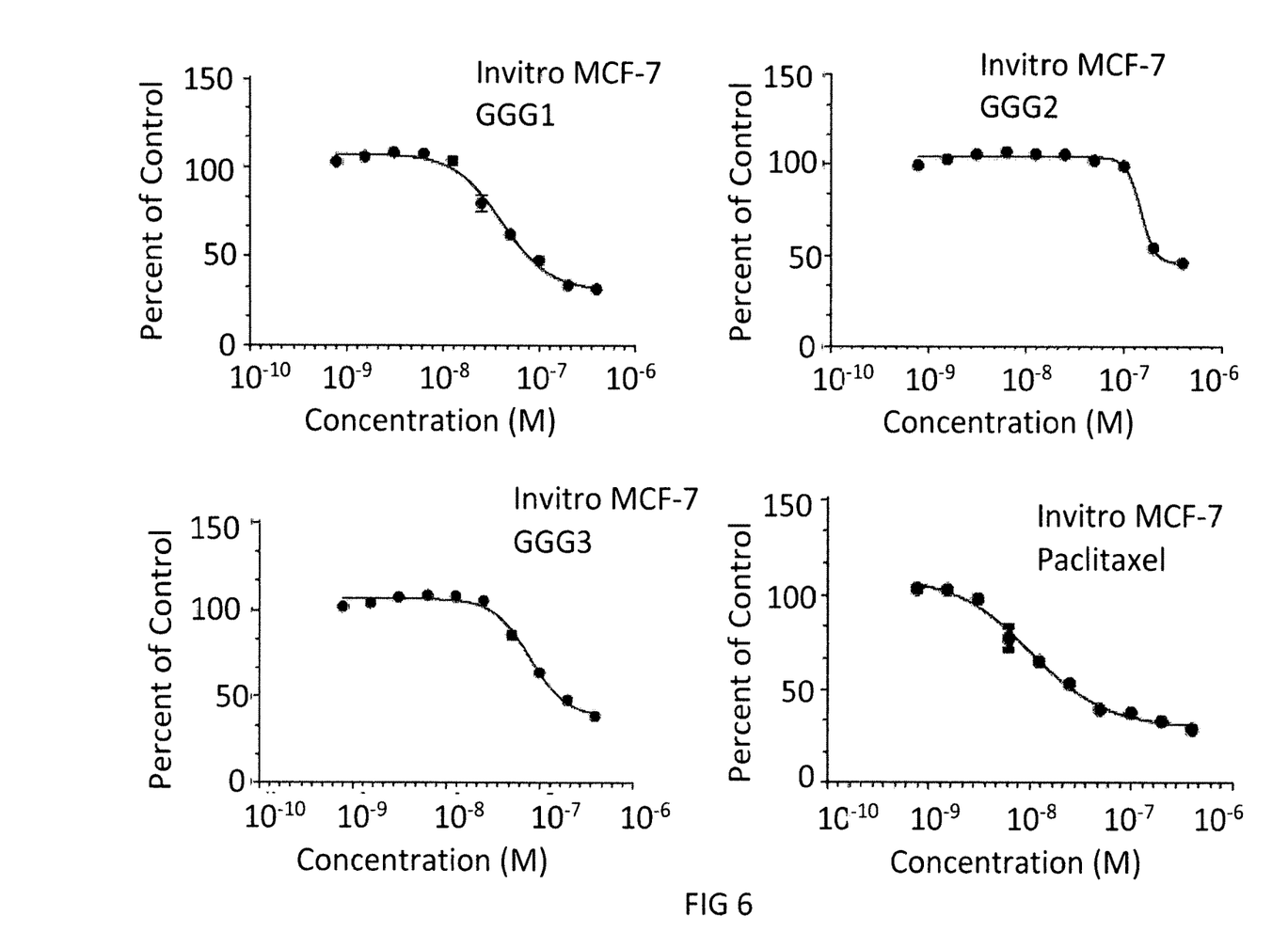
FIG. 6. shows the $IC_{50}$ of human breast cancer MCF-7 cell line for three nanogels encapsulated with paclitaxel and the paclitaxel control.

| MCF-7 cell line | | | | |
|---|---|---|---|---|
| Sample Name | Test ID | $IC_{50}$ | Curve Fit Parameter $R^2$ of fit | Plate Statistics Z' |
| SY2019-CH001 | GGG1 | $4.085 \times 10^{-8}$ | 0.987 | 0.95 |
| SY2019-CH002 | GGG2 | $1.485 \times 10^{-7}$ | 0.989 | 0.95 |
| SY2019-CH003 | GGG3 | $7.931 \times 10^{-8}$ | 0.987 | 0.96 |
| Paclitaxel Control | | $1.06 \times 10^{-9}$ | 0.989 | 0.96 |

While the invention has been described in detail with reference to certain preferred embodiments, it will be understood that modifications and variations are within the spirit and scope of that which is described and claimed.

That which is claimed is:

1. A nanogel particle comprising:
a) a plurality of water-soluble polymers; and
b) a plurality of cyclodextrin derivatives; and
c) the said water-soluble polymers and the said cyclodextrin derivatives are crosslinked by a plurality of covalent bonds, the said covalent bonds comprise at least one sulfur atom; and
d) a plurality of surface molecules, the said surface molecules are conjugated to the surface of the said nanogel particle by a plurality of covalent bonds;

The average particle size of the said nanogel particle is less than 1000 nanometers, the said nanogel particle is monodispersed having a polydispersity index of equal to or less than 0.3.

2. The nanogel particle of claim 1, wherein the said covalent bonds are thiol ether bonds.

3. The nanogel particle of claim 1, wherein the said covalent bonds are disulfide bonds.

4. The nanogel particle of claim 1, wherein the said covalent bonds are disulfide bonds and thiol ether bonds.

5. The nanogel particle of claim 1, wherein the said nanogel particle comprises at least one biodegradable bond.

6. The nanogel particle of claim 1, wherein the said nanogel particle comprises at least one biologically active agent encapsulated in the said nanogel particle.

7. The nanogel particle of claim 1, wherein the average particle size of the said nanogel particle is 30-100 nm.

8. The nanogel particle of claim 1, wherein the average particle size of the said nanogel particle is 30-200 nm.

9. The nanogel particle of claim 1, wherein average particle size of the said nanogel particle is 100-200 nm.

10. The nanogel particle of claim 1, wherein the said surface molecules are targeting ligands.

11. The nanogel particle of claim 10, wherein the said targeting ligands are targeting ligands for cancer cells.

12. The nanogel particle of claim 11, wherein the said targeting ligands for cancer cells are folates.

13. The nanogel particle of claim 1, wherein the said surface molecules are dyes.

14. The nanogel particle of claim 13, wherein the said dyes are fluorescent dyes.

15. The nanogel particle of claim 14, wherein the said fluorescent dyes are FITC.

16. The nanogel particle of claim 1, wherein the said biologically active agent is a cancer chemotherapy agent.

17. The nanogel particle of claim 16, wherein the said cancer chemotherapy agent is paclitaxel.

18. The nanogel particle of claim 1 wherein the said biologically active agent is a dye.

19. The nanogel particle of claim 18, wherein the dye is purpurin.

* * * * *